United States Patent
Ueda et al.

(10) Patent No.: US 11,628,241 B2
(45) Date of Patent: Apr. 18, 2023

(54) BLOOD PURIFICATION APPARATUS

(71) Applicant: NIPRO CORPORATION, Osaka (JP)

(72) Inventors: Mitsutaka Ueda, Osaka (JP); Hidetoshi Saio, Osaka (JP)

(73) Assignee: NIPRO CORPORATION, Osaka (JP)

( * ) Notice: Subject to any disclaimer, the term of this patent is extended or adjusted under 35 U.S.C. 154(b) by 551 days.

(21) Appl. No.: 16/624,944

(22) PCT Filed: Jun. 22, 2018

(86) PCT No.: PCT/JP2018/023907
§ 371 (c)(1),
(2) Date: Dec. 20, 2019

(87) PCT Pub. No.: WO2018/235963
PCT Pub. Date: Dec. 27, 2018

(65) Prior Publication Data
US 2020/0139035 A1    May 7, 2020

(30) Foreign Application Priority Data
Jun. 22, 2017   (JP) .............................. JP2017-122209

(51) Int. Cl.
*A61M 1/16*    (2006.01)
*A61M 1/30*    (2006.01)
*A61M 1/34*    (2006.01)

(52) U.S. Cl.
CPC ............ *A61M 1/1621* (2014.02); *A61M 1/16* (2013.01); *A61M 1/30* (2013.01); *A61M 1/34* (2013.01); *A61M 1/342* (2013.01)

(58) Field of Classification Search
CPC ........ A61M 1/1621; A61M 1/30; A61M 1/34; A61M 1/342; A61M 1/16
See application file for complete search history.

(56) References Cited

U.S. PATENT DOCUMENTS

| | | | |
|---|---|---|---|
| 4,648,866 A | 3/1987 | Malbrancq et al. | |
| 4,687,580 A | 8/1987 | Malbrancq et al. | |

(Continued)

FOREIGN PATENT DOCUMENTS

| | | | |
|---|---|---|---|
| CA | 1207243 A | 7/1986 | |
| CN | 102500005 A | 6/2012 | |

(Continued)

OTHER PUBLICATIONS

International Search Report for PCT/JP2018/023907 dated Sep. 25, 2018 [PCT/ISA/210].

(Continued)

*Primary Examiner* — John Kim
(74) *Attorney, Agent, or Firm* — Sughrue Mion, PLLC

(57) ABSTRACT

A blood purification apparatus that includes a blood purifier, a vascular access flow path, a cleaning solution flow path, and a drainage flow path. The blood purifier has an inner portion divided by a semi-permeable membrane into a first portion and a second portion. The vascular access flow path is connected to the blood purifier and is in communication with the first portion. The cleaning solution flow path is connected to the blood purifier and is in communication with the first portion. The drainage flow path is connected to the blood purifier and is in communication with the second portion. The cleaning solution flow path is provided with a blood pump capable of bidirectionally feeding a fluid. An open-close valve is provided in each of the vascular access flow path and the drainage flow path.

7 Claims, 13 Drawing Sheets

(56) References Cited

U.S. PATENT DOCUMENTS

| | | |
|---|---|---|
| 4,954,128 A | 9/1990 | Ford |
| 5,358,482 A | 10/1994 | Panzani |
| 2011/0098625 A1 | 4/2011 | Masala et al. |
| 2013/0110028 A1 | 5/2013 | Bachmann et al. |
| 2013/0228516 A1 | 9/2013 | Jonsson et al. |
| 2016/0067397 A1 | 3/2016 | Gagel et al. |

FOREIGN PATENT DOCUMENTS

| | | | |
|---|---|---|---|
| CN | 102971023 A | 3/2013 | |
| JP | 58-121956 A | 7/1983 | |
| JP | 62-060562 A | 3/1987 | |
| JP | 64-15060 A | 1/1989 | |
| JP | 03-502061 A | 5/1991 | |
| JP | 2007-020990 A | 2/2007 | |
| JP | 2016-515446 A | 5/2016 | |
| WO | 89/03696 A1 | 5/1989 | |
| WO | 1990/001970 A1 | 3/1990 | |

OTHER PUBLICATIONS

Communication dated Nov. 30, 2021 from the China National Intellectual Property Administration in English Application No. 201880041650.7.
Extended European Search Report dated Feb. 8, 2021 from the European Patent Office in EP Application No. 18819603.4.

BLOOD PURIFICATION APPARATUS

This application is a National Stage of International Application No. PCT/JP2018/023907 filed Jun. 22, 2018, claiming priority based on Japanese Patent Application No. 2017-122209 filed Jun. 22, 2017.

TECHNICAL FIELD

The present invention relates to a blood purification apparatus.

BACKGROUND ART

As a prior art document, Japanese Patent Laying-Open No. 2007-20990 (PTL 1) discloses a configuration of a blood purification apparatus capable of detecting displacement of a vein-side puncture needle. A hemodialysis apparatus disclosed in PTL 1 includes a dialyzer, a blood circuit, a blood pump, a dialysis fluid circuit, and an ultrasonic-type blood flow meter.

CITATION LIST

Patent Literature

PTL 1: Japanese Patent Laying-Open No. 2007-20990

SUMMARY OF INVENTION

Technical Problem

Similarly to the configuration of a commonly used blood purification apparatus, the blood circuit of the hemodialysis apparatus disclosed in PTL 1 is formed of an artery-side blood circuit on the upstream side of the dialyzer and a vein-side blood circuit on the downstream side of the dialyzer so as to form a loop.

In general, a blood purification apparatus is installed in a hospital room narrower than a dialysis room. Thus, such a blood purification apparatus is required to have a simplified apparatus configuration. In the case of a blood purification apparatus in which the above-described loop is formed, needles need to be inserted into each of an artery and a vein, which may increase the burden on patients and medical workers. Also, displacement of a puncture needle may increase the amount of blood loss.

The present invention has been made in light of the above-described problems. An object of the present invention is to provide a blood purification apparatus that has a simplified configuration while still allowing suppression of the amount of blood lost in the case of displacement of a puncture needle.

Solution to Problem

A blood purification apparatus according to the present invention includes a blood purifier, a vascular access flow path, a cleaning solution flow path, and a drainage flow path. The blood purifier has an inner portion divided by a semi-permeable membrane into a first portion and a second portion. The vascular access flow path is connected to the blood purifier and is in communication with the first portion. The cleaning solution flow path is connected to the blood purifier and is in communication with the first portion. The drainage flow path is connected to the blood purifier and is in communication with the second portion. The cleaning solution flow path is provided with a blood pump capable of bidirectionally feeding a fluid. An open-close valve is provided in each of the vascular access flow path and the drainage flow path.

In an embodiment of the present invention, the blood purification apparatus further includes a branch flow path. The branch flow path branches from the cleaning solution flow path and is connected to the blood purifier to allow communication between the cleaning solution flow path and the second portion. An open-close valve is provided in the branch flow path.

In an embodiment of the present invention, the blood purification apparatus further includes a branch flow path. The branch flow path branches from the cleaning solution flow path and is connected to the blood purifier to allow communication between the cleaning solution flow path and the second portion. An open-close valve is provided in a portion of the cleaning solution flow path, the portion being located between the blood purifier and a branch portion that is located between the cleaning solution flow path and the branch flow path.

Advantageous Effects of Invention

According to the present invention, the amount of blood lost in the case of displacement of a puncture needle can be suppressed while simplifying the configuration of the blood purification apparatus.

DESCRIPTION OF EMBODIMENTS

Figure 1:
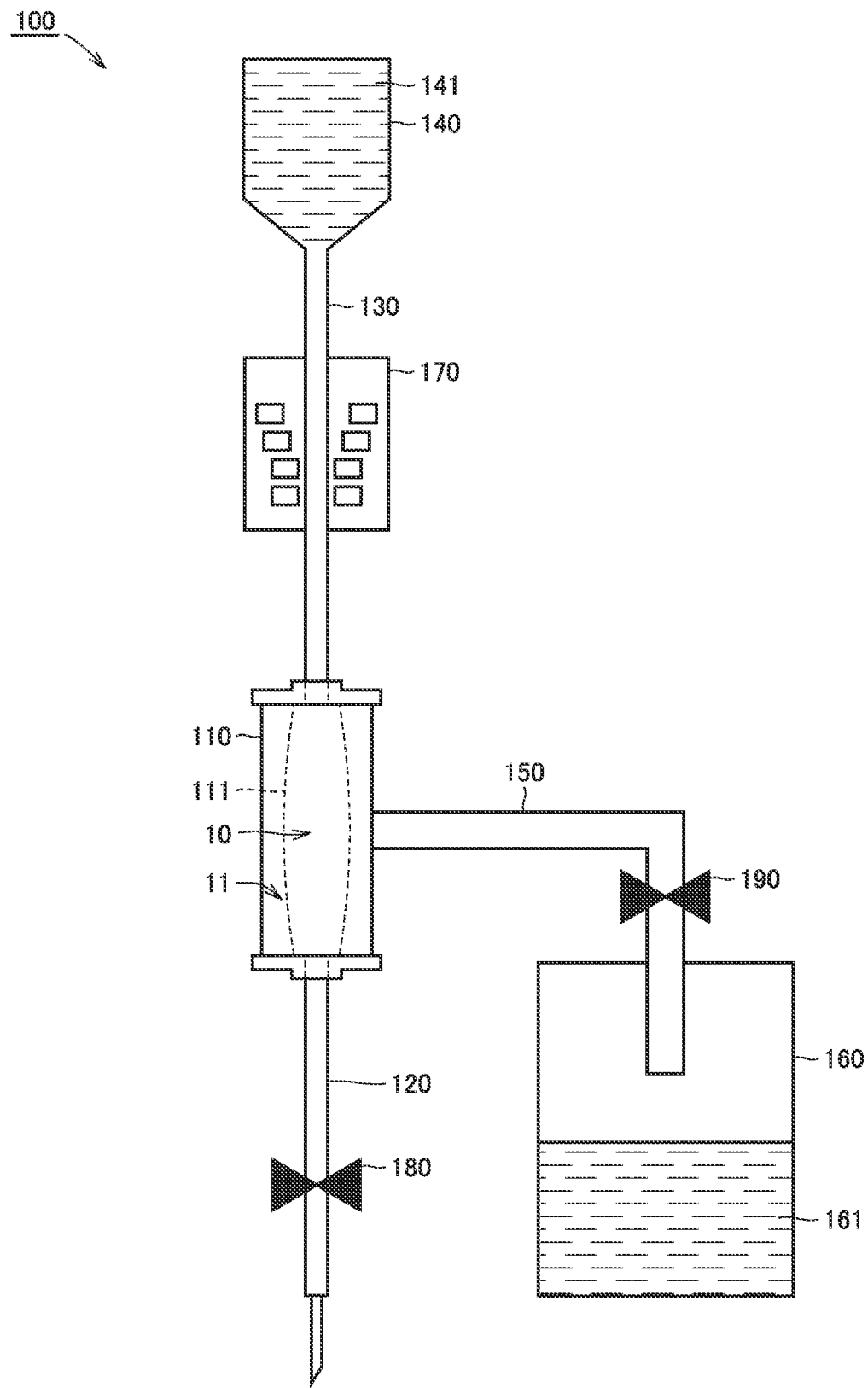
FIG. 1 is a circuit diagram showing the configuration of a blood purification apparatus according to the first embodiment of the present invention.

In the following, a blood purification apparatus according to each of embodiments of the present invention will be described with reference to the accompanying drawings. In the following description of the embodiments, the same or corresponding components will be denoted by the same reference characters, and description thereof will not be repeated.

First Embodiment

FIG. 1 is a circuit diagram showing the configuration of a blood purification apparatus according to the first embodiment of the present invention. As shown in FIG. 1, blood purification apparatus 100 according to the first embodiment of the present invention includes a blood purifier 110, a vascular access flow path 120, a cleaning solution flow path 130, and a drainage flow path 150.

Blood purifier 110 has an inner portion divided, for example, by a semi-permeable membrane 111 such as a hollow fiber membrane into a first portion 10 and a second portion 11. In the present embodiment, the inside space surrounded by semi-permeable membrane 111 corresponds to first portion 10 while the outside space of semi-permeable membrane 111 corresponds to second portion 11.

Vascular access flow path 120 is connected to blood purifier 110 and is in communication with first portion 10. A puncture needle is provided at an end of vascular access flow path 120 on the side opposite to blood purifier 110. Vascular access flow path 120 is provided with a first open-close valve 180 that opens and closes vascular access flow path 120.

Cleaning solution flow path 130 is connected to blood purifier 110 and is in communication with first portion 10. An end of cleaning solution flow path 130 on the side opposite to blood purifier 110 is connected, for example, to a cleaning solution storage portion 140 in which a cleaning solution 141 made of a physiological saline solution or a dialysis fluid is stored. Cleaning solution flow path 130 is provided with a blood pump 170 capable of bidirectionally feeding a fluid.

Drainage flow path 150 is connected to blood purifier 110 and is in communication with second portion 11. An end of drainage flow path 150 on the side opposite to blood purifier 110 is connected to a drainage storage portion 160 in which drainage 161 is stored. Drainage flow path 150 is provided with a second open-close valve 190 that opens and closes drainage flow path 150.

In the following, the operation of blood purification apparatus 100 according to the first embodiment of the present invention will be described.

Before starting dialysis by blood purification apparatus 100, each of blood purifier 110, vascular access flow path 120, cleaning solution flow path 130, and drainage flow path 150 is primed with cleaning solution 141.

Figure 2:
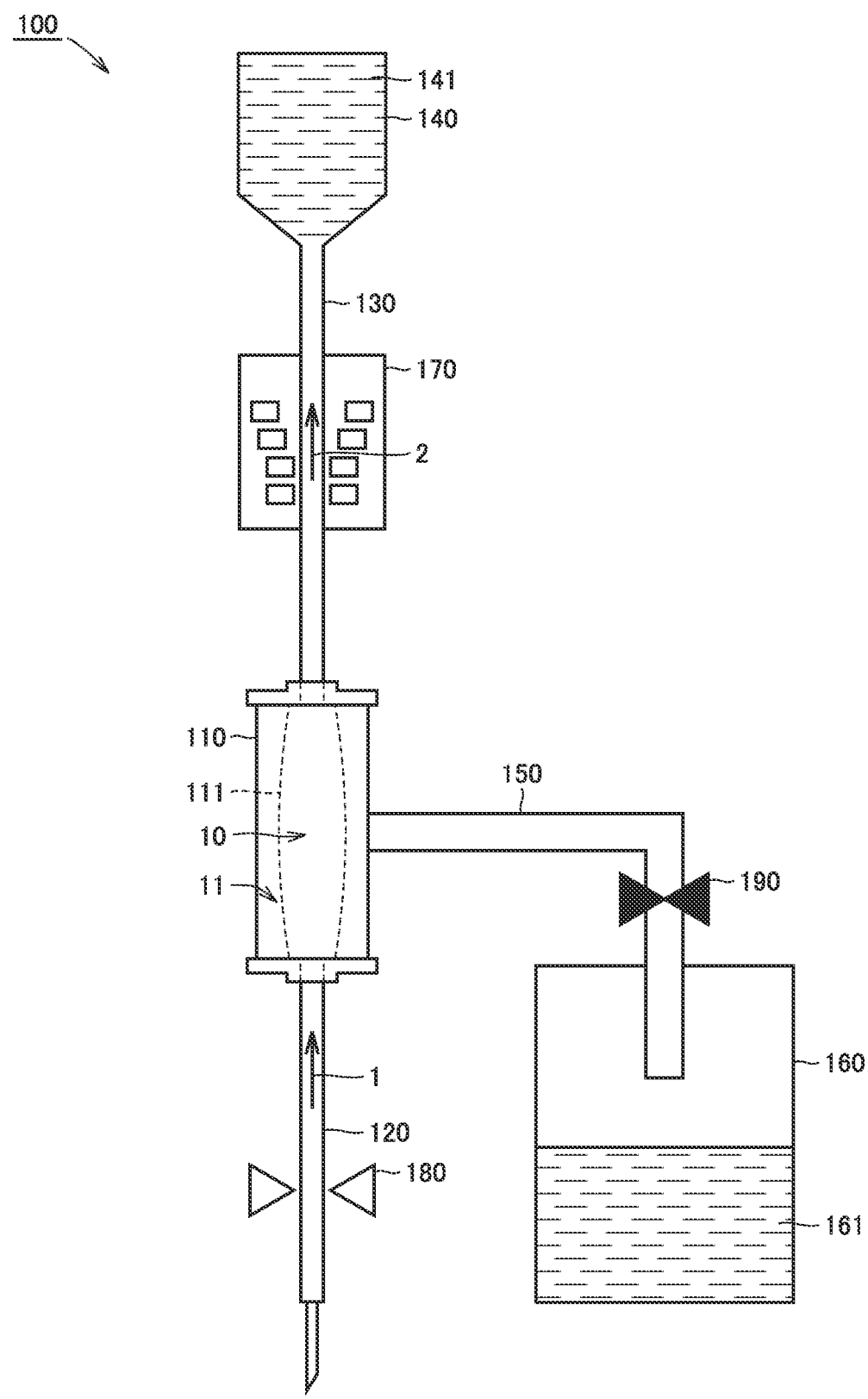
FIG. 2 is a circuit diagram showing a blood removal process in the blood purification apparatus according to the first embodiment of the present invention.

FIG. 2 is a circuit diagram showing a blood removal process in the blood purification apparatus according to the first embodiment of the present invention. As shown in FIG. 2, in the blood removal process in blood purification apparatus 100 according to the first embodiment of the present invention, blood pump 170 feeds a fluid in the suction direction indicated by an arrow 2 in the state where first open-close valve 180 is opened and second open-close valve 190 is closed. As a result, blood flows from vascular access flow path 120 into first portion 10 of blood purifier 110 as indicated by an arrow 1. The blood having passed through first portion 10 of blood purifier 110 flows into cleaning solution flow path 130. In accordance with the amount of the blood having flowed into cleaning solution flow path 130, cleaning solution 141 inside cleaning solution flow path 130 flows into cleaning solution storage portion 140.

Figure 3:
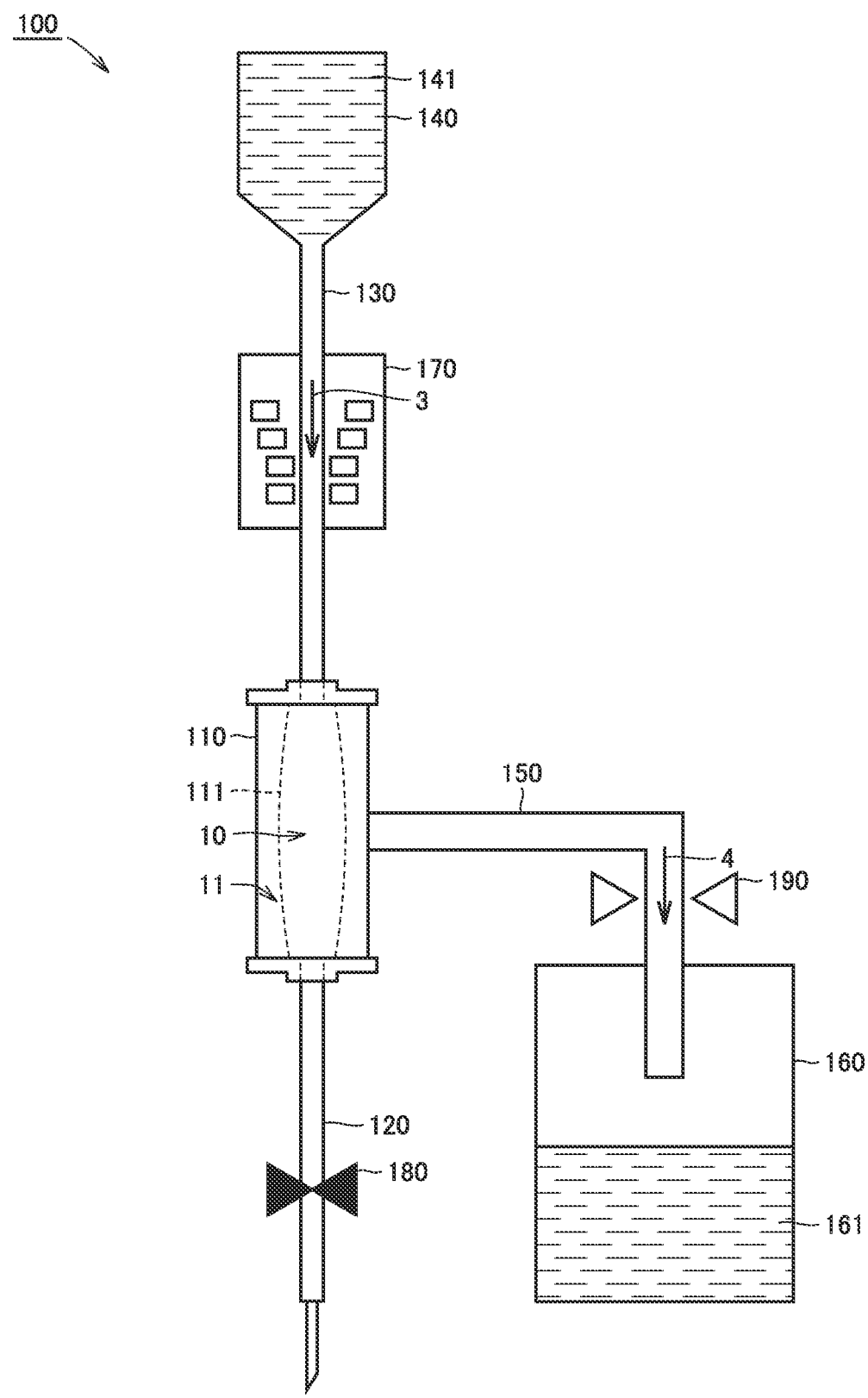
FIG. 3 is a circuit diagram showing a fluid removal process in the blood purification apparatus according to the first embodiment of the present invention.

FIG. 3 is a circuit diagram showing a fluid removal process in the blood purification apparatus according to the first embodiment of the present invention. As shown in FIG. 3, in the fluid removal process in blood purification apparatus 100 according to the first embodiment of the present invention, blood pump 170 feeds a fluid in the drainage direction indicated by an arrow 3 in the state where first open-close valve 180 is closed and second open-close valve 190 is opened.

As a result, the blood in cleaning solution flow path 130 flows into first portion 10 of blood purifier 110. The blood having flowed into first portion 10 of blood purifier 110 is filtered by semi-permeable membrane 111 with the pressure applied from blood pump 170. Drainage 161 having passed through semi-permeable membrane 111 and reached second portion 11 flows into drainage flow path 150 and is stored in drainage storage portion 160. The amount of drainage 161 stored in drainage storage portion 160 is equivalent to the fluid removal amount.

Figure 4:
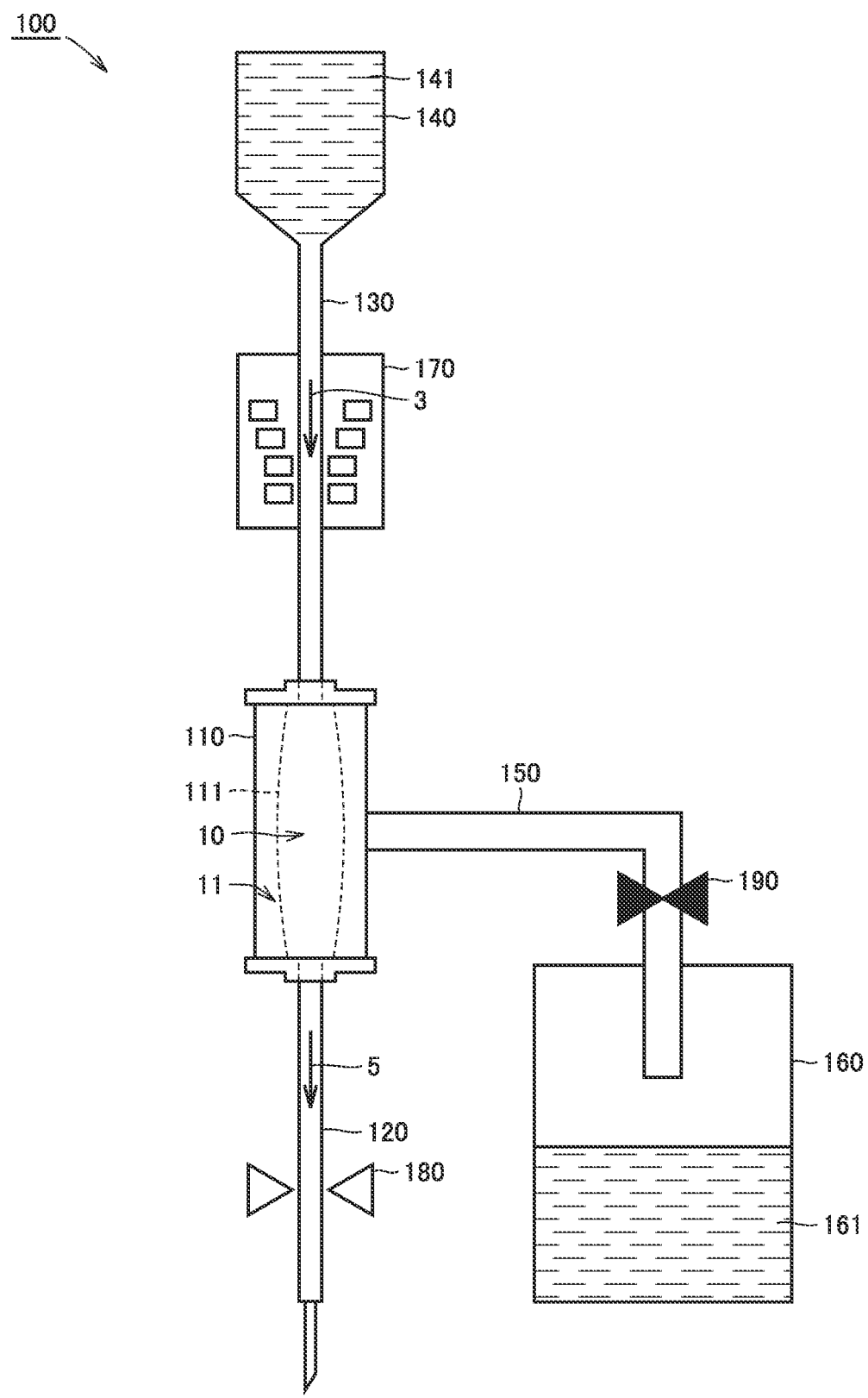
FIG. 4 is a circuit diagram showing a blood returning process in the blood purification apparatus according to the first embodiment of the present invention.

FIG. 4 is a circuit diagram showing a blood returning process in the blood purification apparatus according to the first embodiment of the present invention. As shown in FIG. 4, in the blood returning process in blood purification apparatus 100 according to the first embodiment of the present invention, blood pump 170 feeds a fluid in the drainage direction in the state where first open-close valve 180 is opened and second open-close valve 190 is closed. As a result, the blood from which a fluid is removed in blood purifier 110 flows into vascular access flow path 120 as indicated by an arrow 5 so as to be returned to a patient.

When the fluid removal amount is intentionally increased in the fluid removal process, then in the blood returning process, the patient may supplementarily receive, together with purified blood, cleaning solution 141 by the amount equivalent to the increased amount of the fluid removal amount.

In blood purification apparatus 100 according to the first embodiment of the present invention, the blood removal process and the blood returning process are alternately performed in a simple configuration in which a loop of a blood circuit is not formed. Accordingly, even if a puncture needle is displaced, the amount of blood loss can be suppressed. Specifically, the amount of blood loss can be suppressed to an amount equal to or less than the amount of the blood having flowed into blood purification apparatus 100 in the blood removal process. Furthermore, by inserting a puncture needle only into a vein, blood purification can be performed for a long period of time while relieving the burden on patients.

Second Embodiment

In the following, a blood purification apparatus according to the second embodiment of the present invention will be described with reference to the accompanying drawings. The blood purification apparatus according to the second embodiment of the present invention is different from blood purification apparatus 100 according to the first embodiment mainly in that it further includes a branch flow path. Thus, the description of the same configuration as that of blood purification apparatus 100 will not be repeated.

Figure 5:
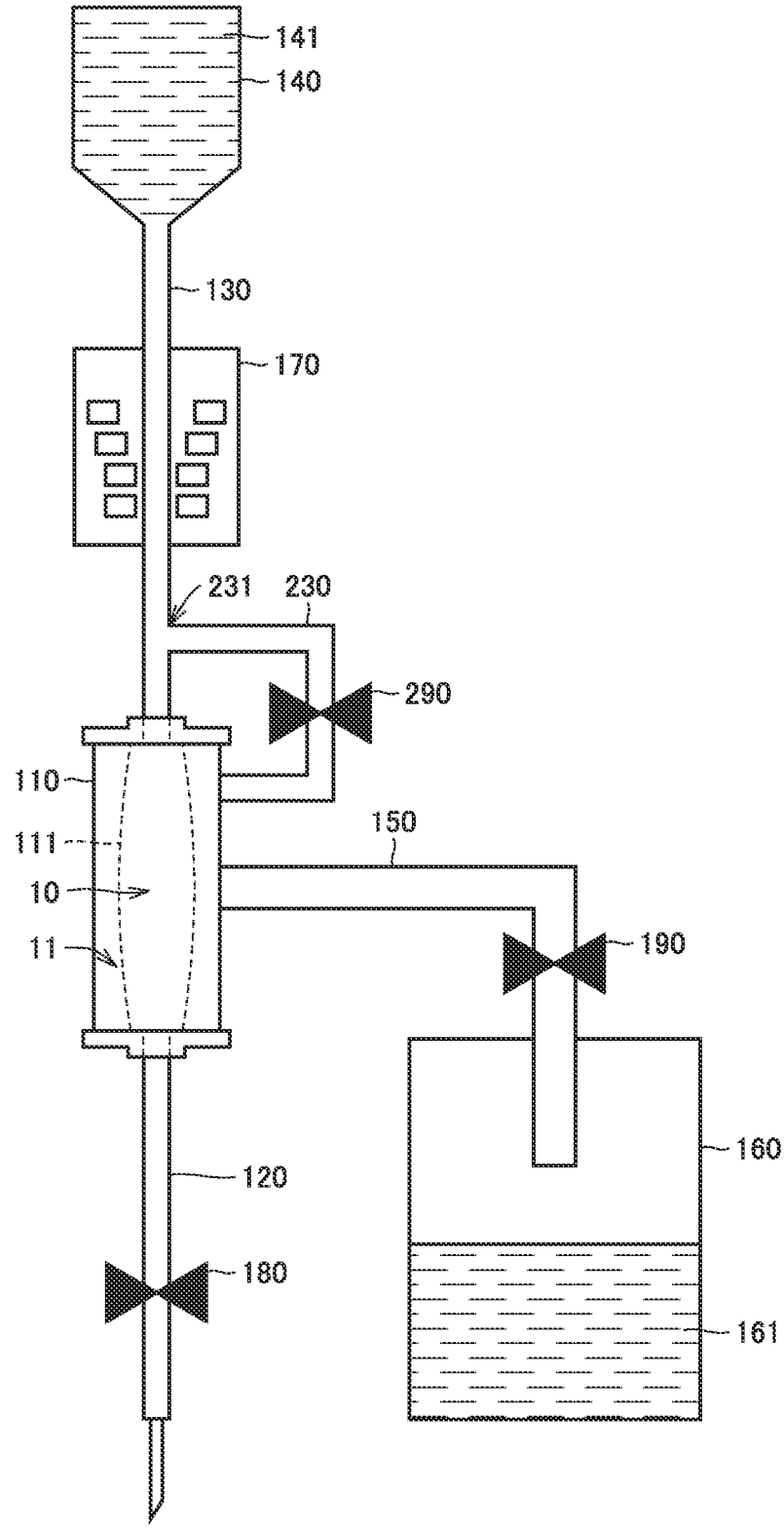
FIG. 5 is a circuit diagram showing the configuration of a blood purification apparatus according to the second embodiment of the present invention.

FIG. 5 is a circuit diagram showing the configuration of a blood purification apparatus according to the second embodiment of the present invention. As shown in FIG. 5, a blood purification apparatus 200 according to the second embodiment of the present invention further includes a branch flow path 230. Branch flow path 230 branches from cleaning solution flow path 130 and is connected to blood purifier 110 so as to allow communication between cleaning solution flow path 130 and second portion 11. Branch flow path 230 is provided with a third open-close valve 290. A branch portion 231 between cleaning solution flow path 130 and branch flow path 230 is provided between blood purifier 110 and blood pump 170.

In the following, the operation of blood purification apparatus 200 according to the second embodiment of the present invention will be described.

Before starting dialysis by blood purification apparatus 200, each of blood purifier 110, vascular access flow path 120, cleaning solution flow path 130, drainage flow path 150, and branch flow path 230 is primed with cleaning solution 141.

Figure 6:
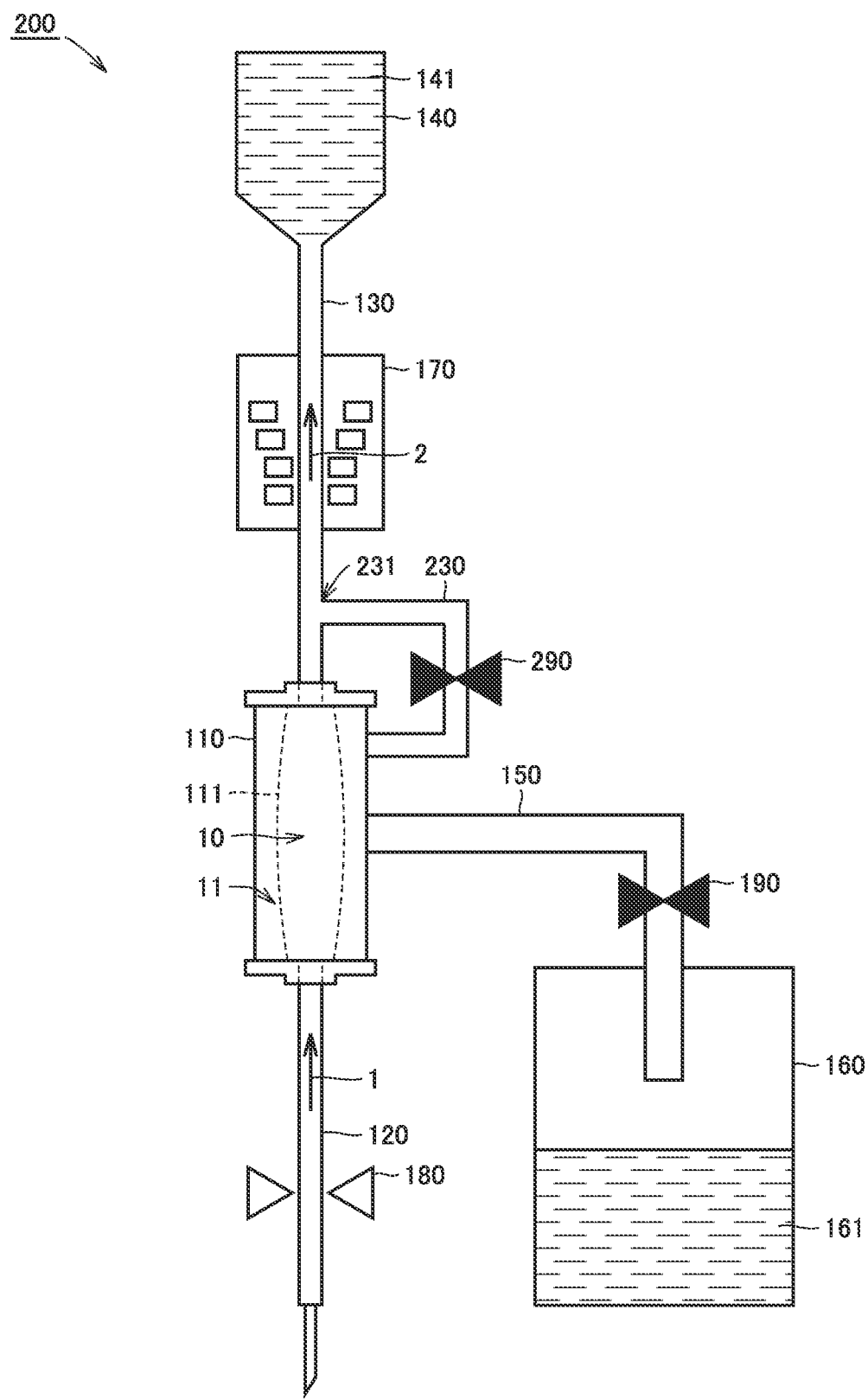
FIG. 6 is a circuit diagram showing a blood removal process in the blood purification apparatus according to the second embodiment of the present invention.

FIG. 6 is a circuit diagram showing a blood removal process in the blood purification apparatus according to the second embodiment of the present invention. As shown in FIG. 6, in the blood removal process in blood purification apparatus 200 according to the second embodiment of the present invention, blood pump 170 feeds a fluid in the suction direction in the state where first open-close valve 180 is opened, second open-close valve 190 is closed, and third open-close valve 290 is closed.

As a result, blood flows from vascular access flow path 120 into first portion 10 of blood purifier 110 as indicated by an arrow 1. The blood having passed through first portion 10 of blood purifier 110 flows into cleaning solution flow path 130. Before the blood reaches branch portion 231, the blood removal process is ended. In other words, the blood is prevented from flowing into branch flow path 230 in the blood removal process.

Figure 7:
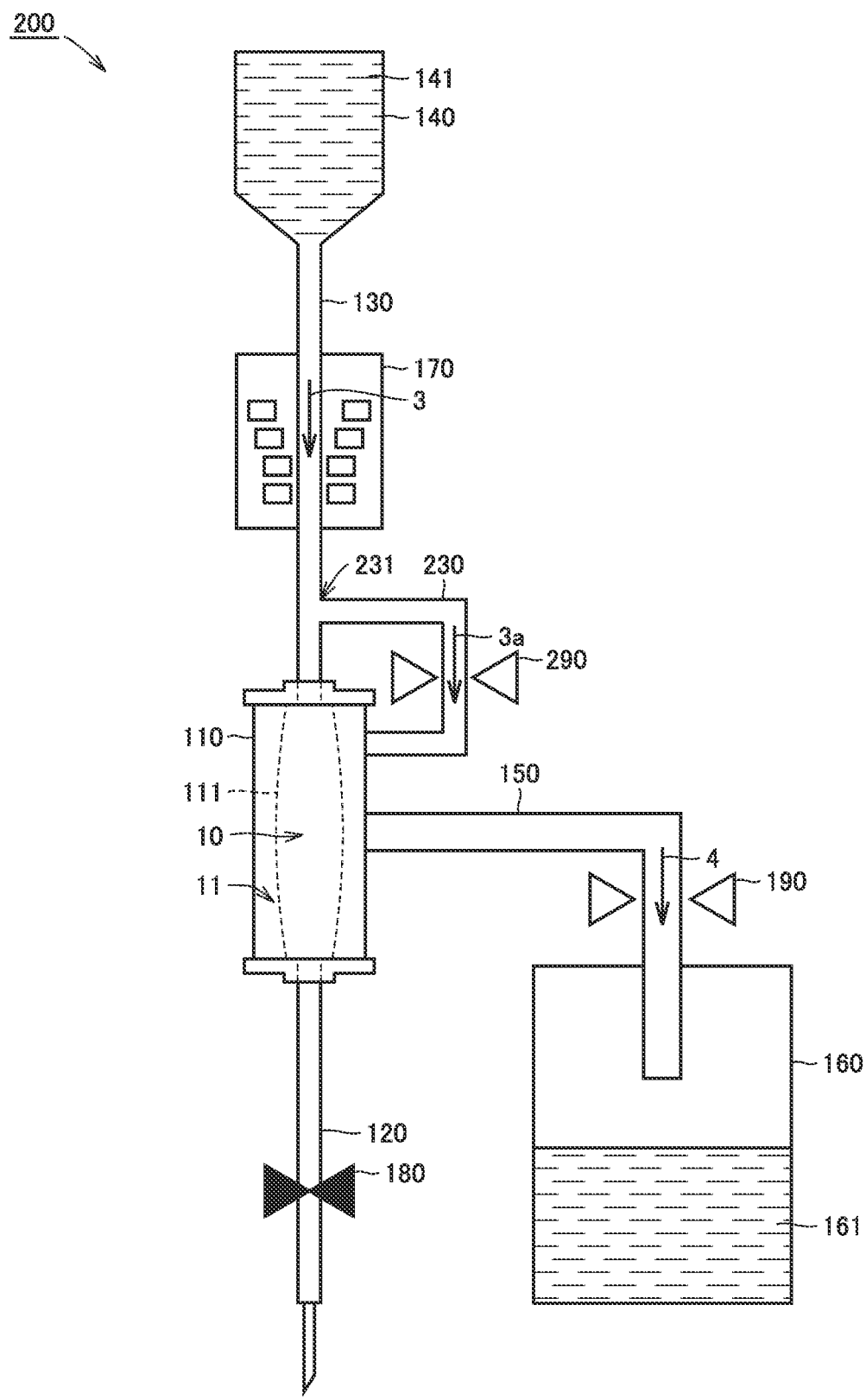
FIG. 7 is a circuit diagram showing a dialysis process in the blood purification apparatus according to the second embodiment of the present invention.

FIG. 7 is a circuit diagram showing the dialysis process in the blood purification apparatus according to the second embodiment of the present invention. As shown in FIG. 7, in the dialysis process in blood purification apparatus 200 according to the second embodiment of the present invention, blood pump 170 feeds a fluid in the drainage direction in the state where first open-close valve 180 is closed, second open-close valve 190 is opened, and third open-close valve 290 is opened.

As a result, the blood in cleaning solution flow path 130 flows into first portion 10 of blood purifier 110. Part of cleaning solution 141 in cleaning solution flow path 130 passes through branch flow path 230 as indicated by an arrow 3a and then flows into second portion 11.

The blood having flowed into first portion 10 of blood purifier 110 comes into contact with cleaning solution 141 in second portion 11 with semi-permeable membrane 111 interposed therebetween. Then, wastes in the blood are moved to second portion 11 by the diffusion principle, so that the blood is purified. Together with the wastes in the blood having passed through semi-permeable membrane 111 and reached second portion 11, cleaning solution 141 having flowed from branch flow path 230 into second portion 11 flows into drainage flow path 150, and then, is stored in drainage storage portion 160.

Figure 8:
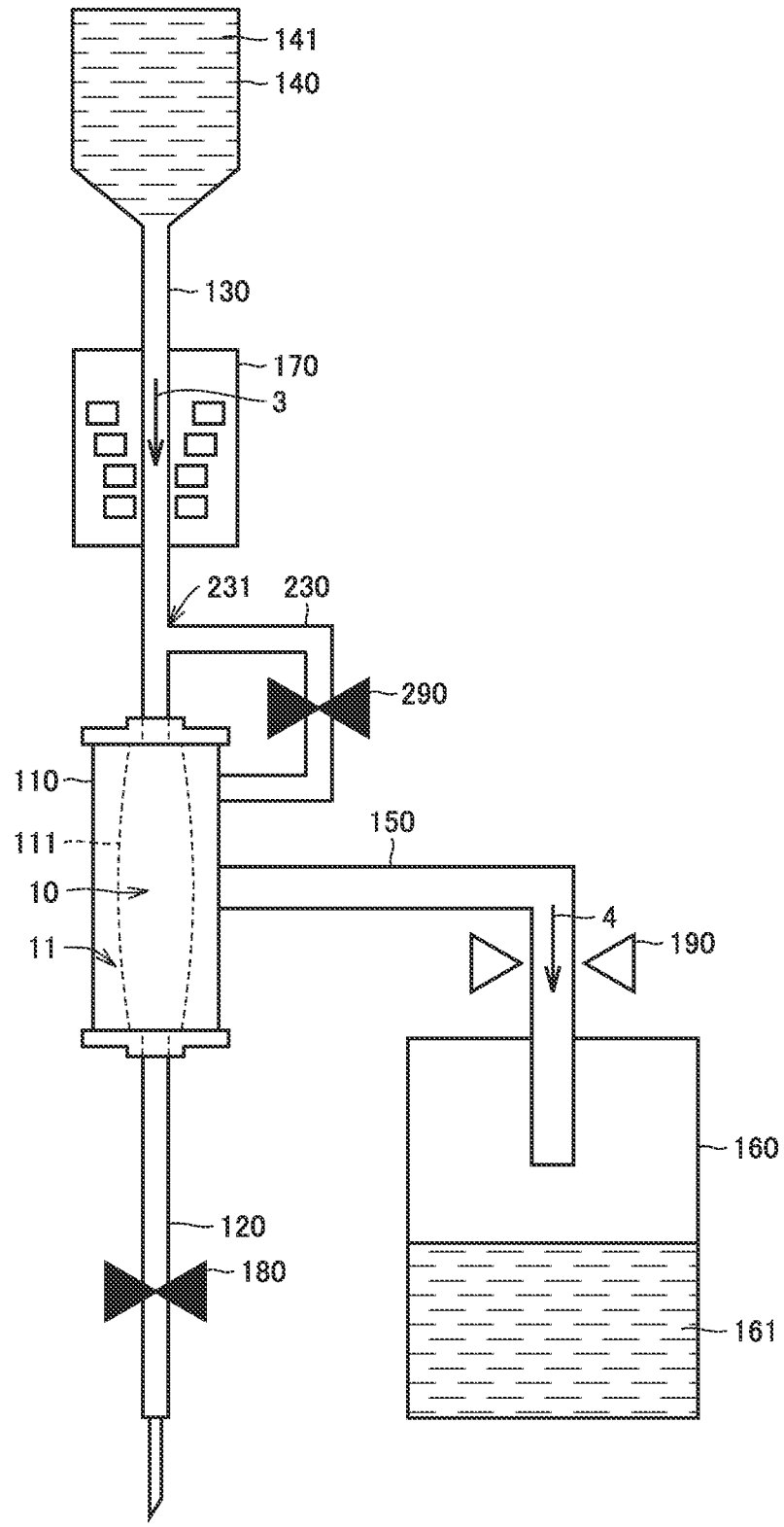
FIG. 8 is a circuit diagram showing a fluid removal process in the blood purification apparatus according to the second embodiment of the present invention.

FIG. 8 is a circuit diagram showing a fluid removal process in the blood purification apparatus according to the second embodiment of the present invention. As shown in FIG. 8, in the fluid removal process in blood purification apparatus 200 according to the second embodiment of the present invention, blood pump 170 feeds a fluid in the drainage direction in the state where first open-close valve 180 is closed, second open-close valve 190 is opened, and third open-close valve 290 is closed.

As a result, the blood in cleaning solution flow path 130 flows into first portion 10 of blood purifier 110. The blood having flowed into first portion 10 of blood purifier 110 is filtered by semi-permeable membrane 111 with the pressure applied from blood pump 170. Drainage 161 having passed through semi-permeable membrane 111 and reached second portion 11 flows into drainage flow path 150, and then, is stored in drainage storage portion 160.

Figure 9:
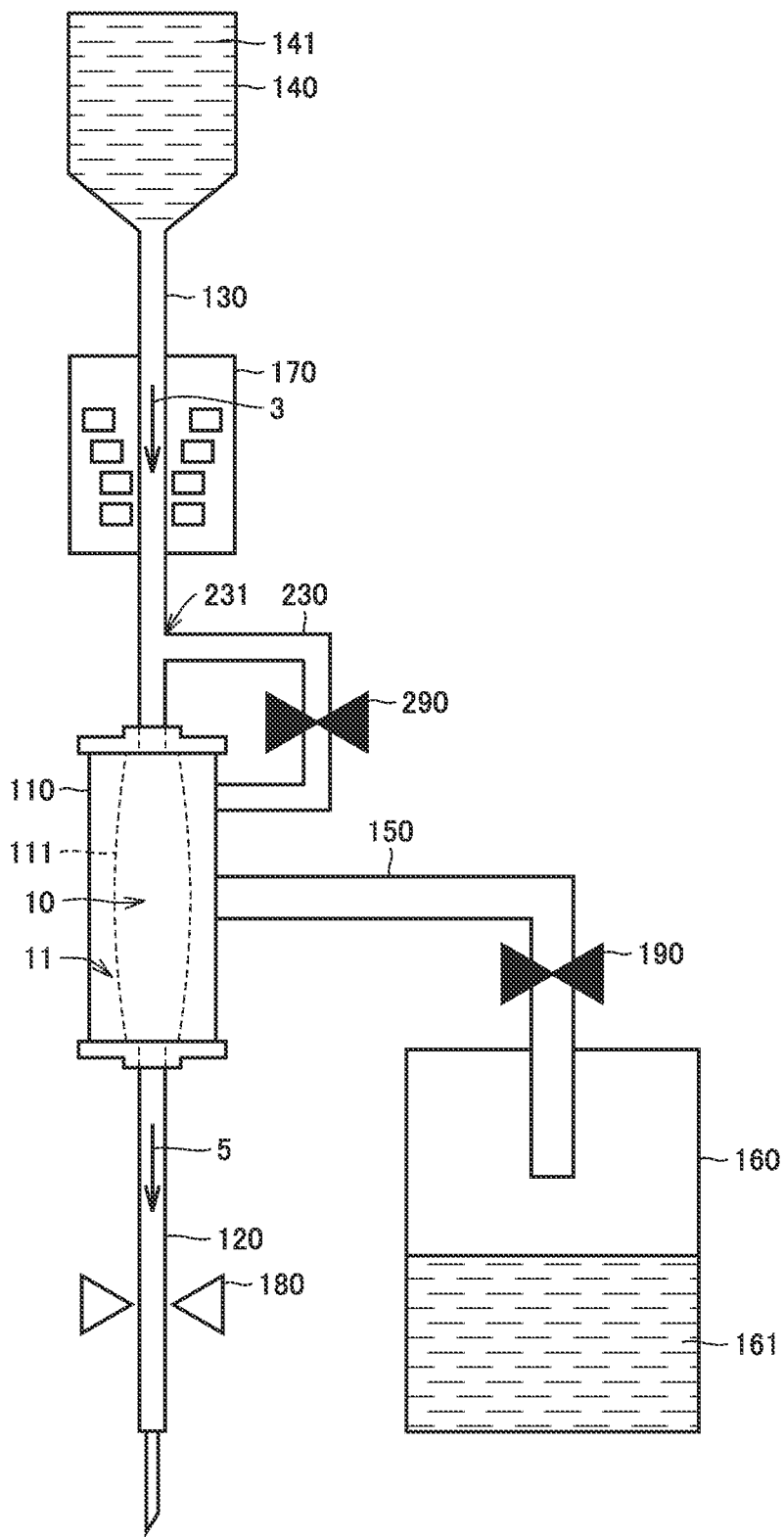
FIG. 9 is a circuit diagram showing a blood returning process in the blood purification apparatus according to the second embodiment of the present invention.

FIG. 9 is a circuit diagram showing a blood returning process in the blood purification apparatus according to the second embodiment of the present invention. As shown in FIG. 9, in the blood returning process in blood purification apparatus 200 according to the second embodiment of the present invention, blood pump 170 feeds a fluid in the drainage direction in the state where first open-close valve 180 is opened, second open-close valve 190 is closed, and third open-close valve 290 is closed. As a result, the blood purified in blood purifier 110 flows into vascular access flow path 120 as indicated by an arrow 5, so as to be returned to a patient.

Also in blood purification apparatus 200 according to the second embodiment of the present invention, the blood removal process and the blood returning process are alternately performed in a simple configuration in which a loop of a blood circuit is not formed. Accordingly, even if a puncture needle is displaced, the amount of blood loss can be suppressed. Specifically, the amount of blood loss can be suppressed to an amount equal to or less than the amount of the blood having flowed into blood purification apparatus 200 in the blood removal process.

Also, in the blood returning process, blood pump 170 may feed a fluid in the drainage direction in the state where first open-close valve 180 is opened, second open-close valve 190 is closed, and third open-close valve 290 is opened. In this case, the solution located in second portion 11 is reverse-filtered by semi-permeable membrane 111 with the pressure applied from blood pump 170.

Third Embodiment

In the following, a blood purification apparatus according to the third embodiment of the present invention will be described with reference to the accompanying drawings. The blood purification apparatus according to the third embodiment of the present invention is different from blood purification apparatus 200 according to the second embodiment mainly in the position where an open-close valve is provided. Thus, the description of the same configuration as that of blood purification apparatus 200 will not be repeated.

Figure 10:
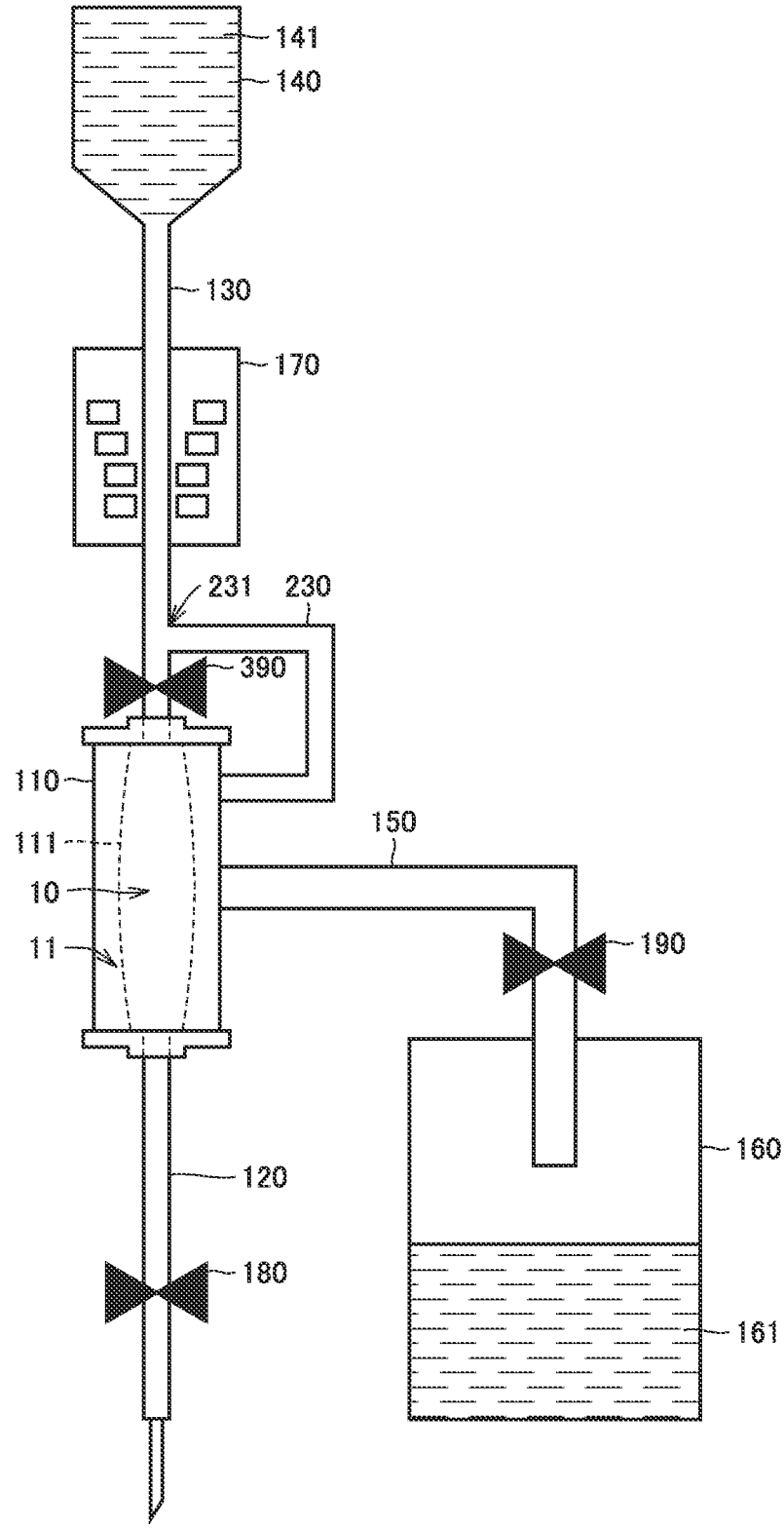
FIG. 10 is a circuit diagram showing the configuration of a blood purification apparatus according to the third embodiment of the present invention.

FIG. 10 is a circuit diagram showing the configuration of a blood purification apparatus according to the third embodiment of the present invention. As shown in FIG. 10, in a blood purification apparatus 300 according to the third embodiment of the present invention, a fourth open-close valve 390 is provided in place of third open-close valve 290. Fourth open-close valve 390 is provided in a portion of cleaning solution flow path 130, the portion being located between blood purifier 110 and branch portion 231 that is located between cleaning solution flow path 130 and branch flow path 230. It should be noted that both third open-close valve 290 and fourth open-close valve 390 may be provided.

In the following, the operation of blood purification apparatus 300 according to the third embodiment of the present invention will be described.

Before starting dialysis by blood purification apparatus 300, each of blood purifier 110, vascular access flow path 120, cleaning solution flow path 130, drainage flow path 150, and branch flow path 230 is primed with cleaning solution 141.

Figure 11:
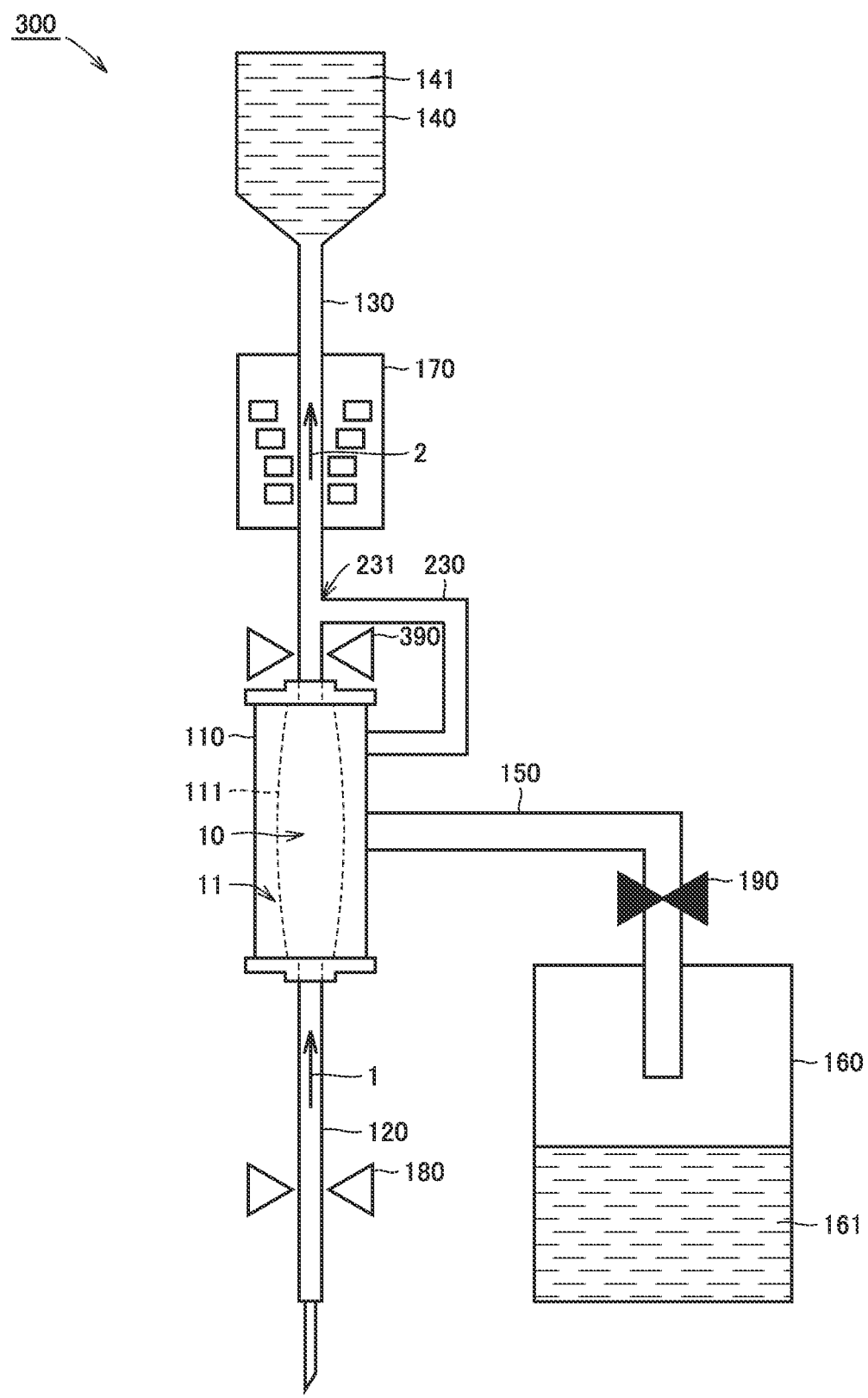
FIG. 11 is a circuit diagram showing a blood removal process in the blood purification apparatus according to the third embodiment of the present invention.

FIG. 11 is a circuit diagram showing a blood removal process in the blood purification apparatus according to the third embodiment of the present invention. As shown in FIG. 11, in the blood removal process in blood purification apparatus 300 according to the third embodiment of the present invention, blood pump 170 feeds a fluid in the suction direction in the state where first open-close valve 180 is opened, second open-close valve 190 is closed, and fourth open-close valve 390 is opened.

As a result, blood flows into first portion 10 of blood purifier 110 from vascular access flow path 120 as indicated by an arrow 1. The blood having passed through first portion 10 of blood purifier 110 flows into cleaning solution flow path 130. It should be noted that the blood removal process is ended before the blood reaches branch portion 231. In other words, the blood is prevented from flowing into branch flow path 230 in the blood removal process.

Figure 12:
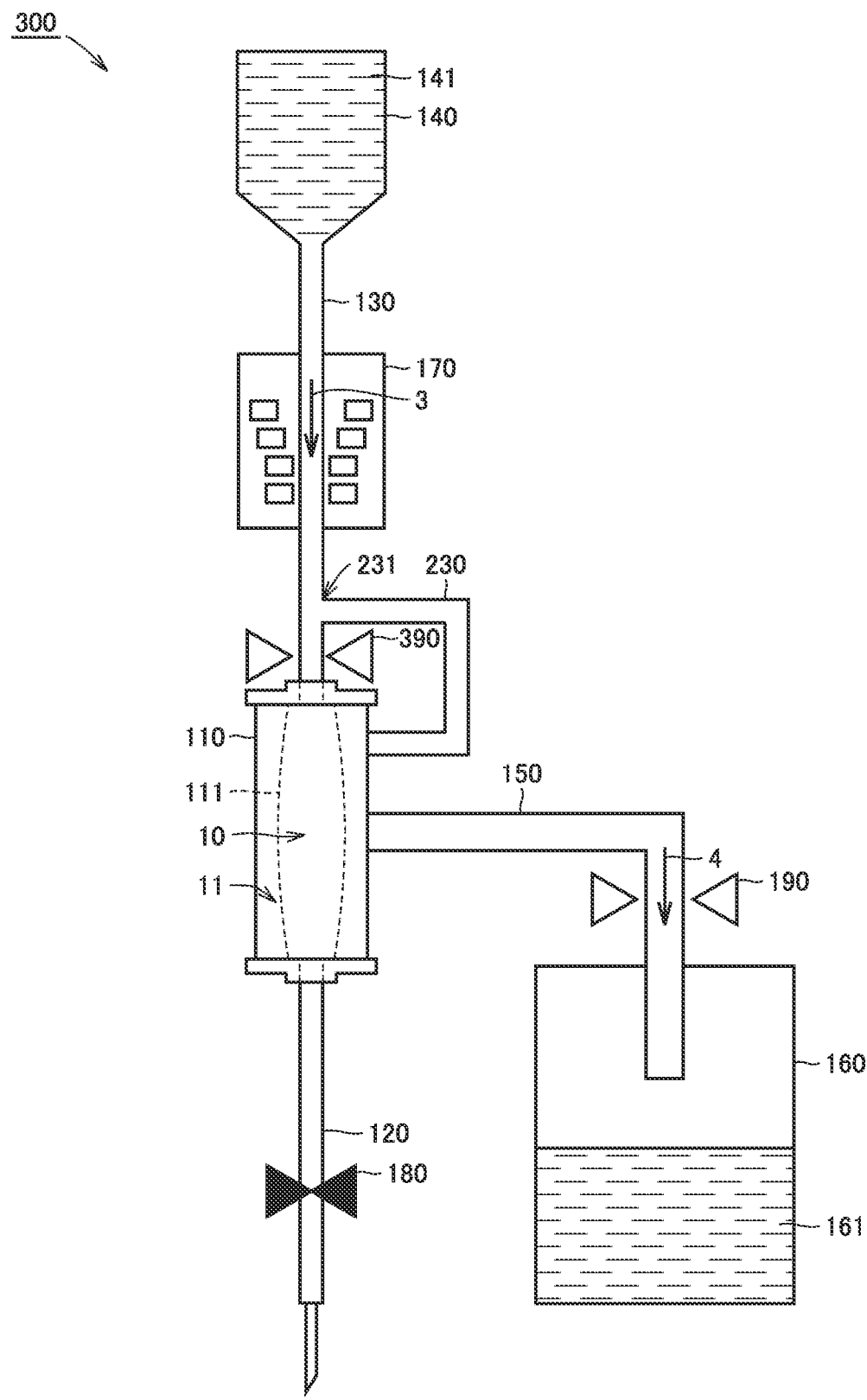
FIG. 12 is a circuit diagram showing a fluid removal process in the blood purification apparatus according to the third embodiment of the present invention.

FIG. 12 is a circuit diagram showing a fluid removal process in the blood purification apparatus according to the third embodiment of the present invention. As shown in FIG. 12, in the fluid removal process in blood purification apparatus 300 according to the third embodiment of the present invention, blood pump 170 feeds a fluid in the drainage direction in the state where first open-close valve 180 is closed, second open-close valve 190 is opened, and fourth open-close valve 390 is opened.

As a result, the blood in cleaning solution flow path 130 flows into first portion 10 of blood purifier 110. The blood having flowed into first portion 10 of blood purifier 110 is filtered by semi-permeable membrane 111 with the pressure applied from blood pump 170. Drainage 161 having passed through semi-permeable membrane 111 and reached second portion 11 flows into drainage flow path 150, and then, is stored in drainage storage portion 160.

Figure 13:
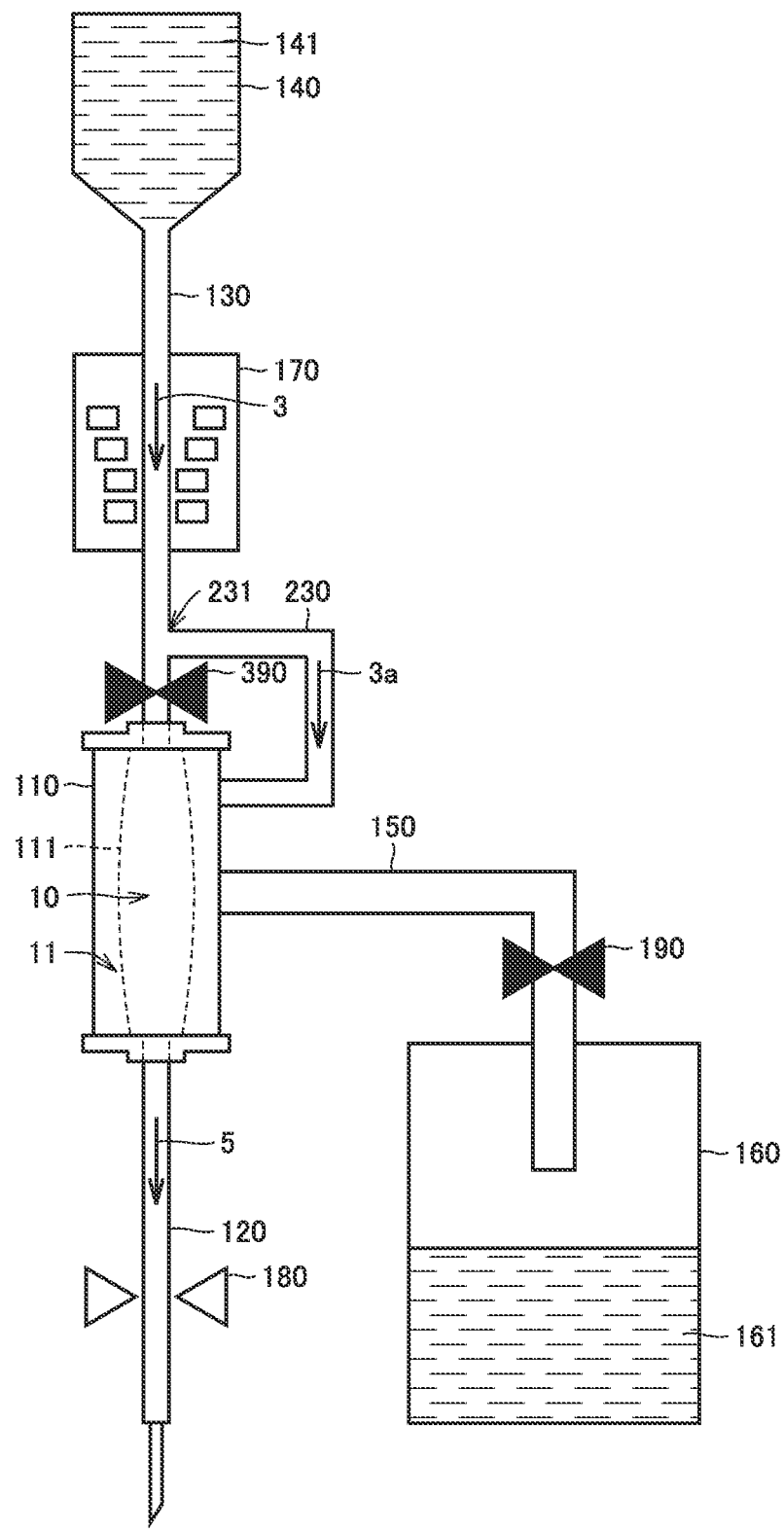
FIG. 13 is a circuit diagram showing a blood returning process in the blood purification apparatus according to the third embodiment of the present invention.

FIG. 13 is a circuit diagram showing a blood returning process in the blood purification apparatus according to the third embodiment of the present invention. As shown in FIG. 13, in the blood returning process in blood purification apparatus 300 according to the third embodiment of the present invention, blood pump 170 feeds a fluid in the drainage direction in the state where first open-close valve 180 is opened, second open-close valve 190 is closed, and fourth open-close valve 390 is closed. As a result, the solution located in second portion 11 is reverse-filtered by semi-permeable membrane 111 with the pressure applied from blood pump 170. Also, the blood purified in blood purifier 110 flows into vascular access flow path 120 as indicated by an arrow 5 so as to be returned to a patient.

Also in blood purification apparatus 300 according to the third embodiment of the present invention, the blood removal process and the blood returning process are alternately performed in a simple configuration in which a loop of a blood circuit is not formed. Accordingly, even if a puncture needle is displaced, the amount of blood loss can be suppressed. Specifically, the amount of blood loss can be suppressed to an amount equal to or less than the amount of the blood having flowed into blood purification apparatus 300 in the blood removal process.

It is noted that the embodiments disclosed herein are illustrative in every respect, and do not provide grounds for restrictive interpretation. Therefore, the technical scope of the present invention should not be interpreted by the above embodiments only, and is defined based on the description in the scope of the claims. Further, any modifications within the meaning and scope equivalent to the scope of the claims are encompassed.

REFERENCE SIGNS LIST 10 first portion, 11 second portion, 100, 200, 300 blood purification apparatus, 110 blood purifier, 111 semi-permeable membrane, 120 vascular access flow path, 130 cleaning solution flow path, 140 cleaning solution storage portion, 141 cleaning solution, 150 drainage flow path, 160 drainage storage portion, 161 drainage, 170 blood pump, 180 first open-close valve, 190 second open-close valve, 230 branch flow path, 231 branch portion, 290 third open-close valve, 390 fourth open-close valve.

The invention claimed is:

1. A blood purification apparatus comprising:
   a blood purifier that has an inner portion divided by a semi-permeable membrane into a first portion and a second portion;
   a vascular access flow path that is connected to the blood purifier and is in communication with the first portion;
   a cleaning solution flow path that is connected to the blood purifier and is in communication with the first portion;
   a drainage flow path that is connected to the blood purifier and is in communication with the second portion; and
   a cleaning solution storage portion connected to the cleaning solution flow path on a side opposite to the blood purifier, wherein
   the cleaning solution flow path is provided with a blood pump capable of bidirectionally feeding a fluid,
   a first open-close valve is provided in the vascular access flow path and a second open-close valve is provided in the drainage flow path, and
   the cleaning solution storage portion is filled with a physiological saline solution or a dialysis fluid.

2. A blood purification apparatus comprising:
   a blood purifier that has an inner portion divided by a semi-permeable membrane into a first portion and a second portion;
   a vascular access flow path that is connected to the blood purifier and is in communication with the first portion;
   a cleaning solution flow path that is connected to the blood purifier and is in communication with the first portion; and
   a drainage flow path that is connected to the blood purifier and is in communication with the second portion, wherein
   the cleaning solution flow path is provided with a blood pump capable of bidirectionally feeding a fluid, and
   a first open-close valve is provided in the vascular access flow path and a second open-close valve is provided in the drainage flow path,
   the apparatus further comprising a branch flow path that branches from the cleaning solution flow path and is connected to the blood purifier to allow communication between the cleaning solution flow path and the second portion, wherein a third open-close valve is provided in the branch flow path.

3. The blood purification apparatus according to claim 2, further comprising a cleaning solution storage portion connected to the cleaning solution flow path on a side opposite to the blood purifier.

4. The blood purification apparatus according to claim 3, wherein the cleaning solution storage portion is filled with a physiological saline solution or a dialysis fluid.

5. A blood purification apparatus comprising:
a blood purifier that has an inner portion divided by a semi-permeable membrane into a first portion and a second portion;
a vascular access flow path that is connected to the blood purifier and is in communication with the first portion;
a cleaning solution flow path that is connected to the blood purifier and is in communication with the first portion; and
a drainage flow path that is connected to the blood purifier and is in communication with the second portion, wherein
the cleaning solution flow path is provided with a blood pump capable of bidirectionally feeding a fluid, and
a first open-close valve is provided in the vascular access flow path and a second open-close valve is provided in the drainage flow path,
the apparatus further comprising a branch flow path that branches from the cleaning solution flow path and is connected to the blood purifier to allow communication between the cleaning solution flow path and the second portion, wherein
a third open-close valve is provided in a portion of the cleaning solution flow path, the portion being located between the blood purifier and a branch portion that is located between the cleaning solution flow path and the branch flow path.

6. The blood purification apparatus according to claim 5, further comprising a cleaning solution storage portion connected to the cleaning solution flow path on a side opposite to the blood purifier.

7. The blood purification apparatus according to claim 6, wherein the cleaning solution storage portion is filled with a physiological saline solution or a dialysis fluid.

* * * * *